United States Patent [19]

Wallace

[11] 4,018,231

[45] * Apr. 19, 1977

[54] DISPOSABLE BALLOON TYPE CATHETER

[75] Inventor: Dean R. Wallace, Fort Myers, Fla.

[73] Assignee: Airco, Inc., Montvale, N.J.

[ * ] Notice: The portion of the term of this patent subsequent to Aug. 26, 1992, has been disclaimed.

[22] Filed: June 2, 1975

[21] Appl. No.: 583,314

Related U.S. Application Data

[63] Continuation-in-part of Ser. No. 436,314, Jan. 24, 1974, Pat. No. 3,901,246.

[52] U.S. Cl. .............................. 128/351; 128/349 B
[51] Int. Cl.² ......................................... A61M 25/00
[58] Field of Search ........ 128/351, 349 B, 349 BV, 128/348, 350 R, 246, 344

[56] References Cited

UNITED STATES PATENTS

| | | | |
|---|---|---|---|
| 2,308,484 | 1/1943 | Auzin et al. | 128/349 B X |
| 2,330,399 | 9/1943 | Winder | 128/349 B |
| 2,845,930 | 8/1958 | Brown | 128/348 |
| 3,407,817 | 10/1968 | Galleher | 128/351 |
| 3,848,605 | 11/1974 | Penny et al. | 128/351 |
| 3,896,816 | 7/1975 | Mattler | 128/349 B |
| 3,901,246 | 8/1975 | Wallace | 128/351 |

Primary Examiner—Dalton L. Truluck
Attorney, Agent, or Firm—Roger M. Rathbun; Edmund W. Bopp; H. Hume Mathews

[57] ABSTRACT

A tracheal tube adapted for insertion into the trachea of a patient for introducing or removing gas. The tube includes a main inflatable cuff which surrounds the distal end of the tube. A gas passageway communicates at one end with the interior of the cuff, and the other end of the passageway is adapted to receive an inflating means, for delivering gas to inflate the cuff. The gas passageway includes a check valve, and a generally oval pilot balloon is in gas communication with the cuff via the passageway. The pilot balloon is longitudinally pre-stretched between its opposite end portions by means maintaining the pre-stretched condition. Accordingly the balloon in its non-inflated condition is characterized by a series of mutually spaced folds, extending longitudinally between the opposed ends. The ridges of the folds contrast with the troughs between folds, to provide a series of spaced, visually discernible markings which visually signal the non-inflated condition of the main cuff. The cuff itself is preferably pre-stretched between its secured ends, so that it, like the pilot balloon, is characterized in the non-inflated state by longitudinally extending folds. The main cuff is thus substantially free of transversely-oriented folds, in consequence of which the cuff is streamlined in the direction of tracheal insertion, to facilitate such operation.

6 Claims, 5 Drawing Figures

DISPOSABLE BALLOON TYPE CATHETER

This application is a continuation-in-part of my copending application, Ser. No. 436,314, filed Jan. 24, 1974, now U.S. Pat. No. 3,901,246 issued Aug. 8, 1975, for BALLOON TRACHEAL CATHETER WITH INFLATION VALVE AND INDICATOR.

BACKGROUND OF INVENTION

This invention relates to balloon-type catheters or endotracheal tubes designed for insertion into a patient for introduction of gases to the patient. Such catheters are commonly inserted into a patient's trachea, or windpipe, and include an inflatable balloon or cuff at the distal end which, when inflated, retains the catheter in position and seals the catheter against the internal wall of the trachea.

At the present time, it is common commercial practice to provide disposable catheters of the type herein described. Such tubes can be used only once and then disposed of, thus eliminating the cost of sterilizing to prevent cross-infection. The practical value of disposability, of course, depends greatly upon the cost of producing and marketing the disposable tubes. Such tubes, therefore, should be capable of rapid mass production manufacturing techniques, yet the resultant catheter must, of course, be of fool-proof design so that mass production cannot give rise to the possibility of a failure or defect in the catheter.

In the prior art relevant to endotracheal tubes of the foregoing type, it has occasionally been recognized that the said tubes should preferably be designed as to facilitate rather than impede tube insertion. The significance of this problem is noted, for example, in U.S. Pat. No. 3,862,635, which discloses an endotracheal tube so formed as to define a smooth exterior sliding surface at the distal end of the tube carrying the secured cuff, thereby facilitating the said tube insertion. In the foregoing connection it may be noted that it is most important to assure that the inflatable cuff itself presents no impediment to insertion of the tube into a patient's trachea. It has been found, however, that the prior art cuffs can indeed present an inherent impediment, in that in their deflated conditions the random wrinkling and folding of the cuff can provide projecting portions which can impede the insertion of the cuff — and its subsequent seating against the trachea wall.

In the balloon-type catheters of the present type, the catheter further includes a pilot balloon which is generally joined to the main cuff by a small passageway or lumen and is in series thereto so that the pilot balloon and main cuff inflate and deflate simultaneously. A valve means is provided to control the gas which may be forced into the pilot balloon, and thus, via the lumen, to the main cuff or balloon. The pilot balloon remains exterior of the patient and thus is used as a continuous visual indication as to the inflated or deflated state of the main cuff. This visual indication must be as clear as possible so that there is no doubt to any viewer as to the condition of the main cuff at any time. Present pilot balloons generally are formed in a simple oval shape. Even when the gas pressure within the main cuff is released, a false indication may be gained, in that the pilot balloon appears inflated even when the main cuff is not pressurized. The false indication is attributable to the shape of the pilot balloon or its wall thickness, or both factors.

A further problem in present disposable balloon-type catheters is in the valve itself. The cuff and pilot balloons are preferably inflated by means of a syringe which is inserted into or adjacent the valve and gas is forced from the syringe into the pilot balloon, thence, through the lumen to the main cuff. Various valves are commercially available to serve this purpose. Some are relatively expensive to mass produce in thay they include a plurality of separately manufactured and assembled components while others are not operable by the syringe itself. The disadvantage of the former drawback is economics, while the disadvantage of the latter drawback is that the valves may not operate instantaneous, so that some gas is lost in trying to close off the passageway to the lumen or are cumbersome in actual operation.

In accordance with the forgoing it may be regarded as an object of the present invention to provide a tracheal tube of the type including an inflatable cuff and a pilot balloon, wherein the pilot balloon is so structured as to provide a very positive and highly visual indicator with respect to the condition of inflation of the said cuff.

It is a further object of the present invention, to provide a tracheal tube of the type including an inflatable cuff portion for sealing with the interior of a patient's trachea, wherein the said cuff is so formed as to facilitate insertion of the tube into the patient's trachea, and to facilitate subsequent seating of the cuff with the trachea wall upon cuff expansion.

SUMMARY OF INVENTION

Now in accordance with the present invention, a tracheal tube is provided which is adapted for ready insertion into the trachea of a patient, for introducing or removing gas. The tube of the invention includes a main inflatable cuff which surrounds the distal end thereof. One end of a gas passageway communicates with the interior of the cuff, with the other end of the passageway being adapted to receive an inflating means for delivering gas to inflate the cuff. The gas passageway includes a check valve and a generally oval pilot balloon is in gas communication with the cuff via the said passageway. The pilot balloon is longitudinally pre-stretched between its opposite end portions, by means maintaining the pre-stretched condition. Accordingly, the balloon in its non-inflated condition is characterized by a series of mutually spaced folds extending longitudinally between the opposed end portions. The ridges of the folds contrast with the troughs between folds, to provide a series of spaced, highly visible markings, which visually signal the non-inflated condition of the main cuff. The cuff itself is preferably pre-stretched between secured ends thereof so that it, like the pilot balloon, is characterized in the non-inflated state by longitudinally extending folds. The main cuff because of the pre-stretching, is thus substantially free of transversely oriented folds, in consequence of which the cuff is streamlined in the direction of tracheal insertion, to facilitate such operation.

An improved valve is preferably employed with the invention to control gas for inflation and deflation of the cuff and the pilot balloon. The valve has a minimum of parts and is principally of unitary molded plastic material susceptible of rapid, inexpensive manufacturing procedures. The valve includes an inlet opening which is adpated to receive a syringe for introducing gas to the main valve passageway. The main valve passageway is of a molded flexible material and has at least one radially inwardly directed projection. A blocking plug is retained within the main valve passageway adjacent the projection and normally serves to prevent the passage of gas through the passageway by an interference fit between the periphery of the plug and the interior surface of the main passageway. As a suitable syringe is inserted into the inlet opening, the distal end of the syringe engages the projection and distorts the passageway interior surface radially outward, thus breaking its seal against the periphery of the blocking plug to allow gas forced from the syringe through a bypass then formed about the blocking plug. The gas then can pass by the valve and into the pilot balloon and cuff for inflation thereof. As the syringe is thereafter removed, the flexible main valve passageway returns to its normal position and again seals about the periphery of the plug to again close the main passageway.

The pilot balloon may surround a tubular molded plastic extension and forms a chamber about the extension for inflating the pilot balloon. The molded tubular extension may be molded integral with the valve housing as one piece, and extend entirely through the interior of the pilot balloon so that, during manufacture, the pilot balloon can be stretched before having its ends adhered to the extension. Thus, the finished pilot balloon is pre-stretched, which gives a highly characteristic appearance to the extremely thin plastic balloon material in its deflated condition. The pilot balloon can be inflated in normal fashion and its inflated condition is very apparent in contrast to its deflated or even semi-inflated condition, which is discernible to the eye without any doubt as to its condition.

Since the condition of the pilot balloon assumes the same condition as the cuff within the patient, the precise amount of inflation of the cuff can be easily determined.

The overall valve and pilot balloon unit is very inexpensive to produce due to its unique design. The valve body and tubular extension can be of a single, molded plastic piece and the valve is completed in assembly by the simple insertion of a valve plug into the valve main passageway in an interference fit. Once the plug is inserted it is retained in position and will not dislodge under normal conditions. Thus, the valve can be quickly, efficiently, and inexpensively produced by mass production techniques. The pilot balloon also can be easily added to the tubular extension by pre-stretching the thin flexible pre-molded balloon material and adhering the ends to the extension while retaining the pre-stretched condition.

BRIEF DESCRIPTION OF DRAWINGS

The invention is diagrammatically illustrated, by way of example, in the drawings appended hereto, in which.

DESCRIPTION OF PREFERRED EMBODIMENT

Figure 1:
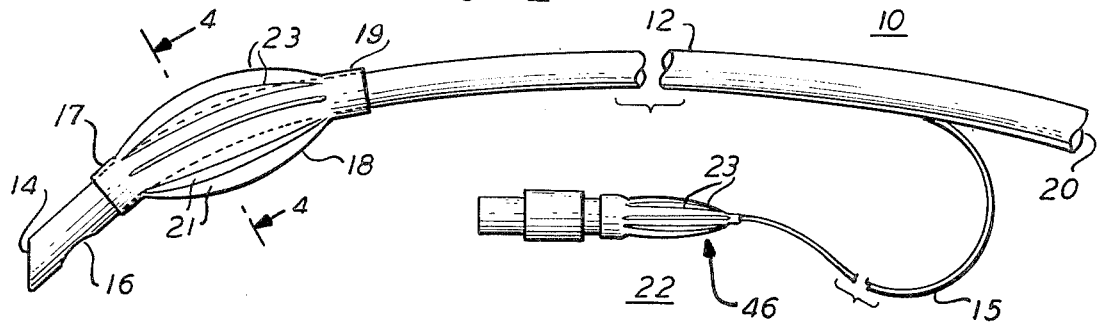
FIG. 1 is a plan view of an endotracheal tube or catheter of the present invention, showing the main cuff at the distal end of the tube and the pilot balloon and valve means.

Referring particularly to FIG. 1, there is shown a disposable balloon-type catheter, or endotracheal tube 10, in accordance with the present invention. The endotracheal tube 10 includes, generally, a plastic tube 12 which is preferably of polyvinyl chloride or other plastic or elastomeric, and has an open distal end 14 including an opening 16 for introducing gas to the patient, and a proximal end (not shown). The main balloon or cuff 18 surrounds tube 12 near the distal end in a gas-tight relationship. Such cuff 18 may be easily made by separately forming the cuff of a thin urethane, vinyl plastic, silicon rubber, or similar material, and sealing its ends 17 and 19 to the desired location along tube 12. Cuff 18, in accordance with the invention is pre-stretched along its length prior to securing ends 17 and 19 — as will be further discussed below. The tube 12 is normally formed in an arcuate configuration for convenience in inserting into the patient's trachea. The main tracheal tube passageway 20 receives gas at its proximal end for induction to the patient through openings 14 and 16.

A secondary passageway (not shown) extends along the length of the tube 12 within the wall thereof and may be formed when the tube 12 itself is formed by extrusion. As an alternate, a separate passageway or lumen may be provided exterior of tube 12. The secondary passageway communicates with the interior of the cuff 18 for inflation of the same. In the preferred form, when the passageway is formed during extrusion within the tube wall, the tube 12 may be slit at any point within the cuff 18 prior to its affixing in position so that the secondary passageway communicates with the interior of cuff 18 for inflation and deflation thereof. The remaining portion of the integral passageway toward the distal end 14 may be sealed during formation of the distal end 14 by heat sealing.

In the preferred embodiment, as shown, a small capillary tube 15 joins the integral passageway to the inflating means shown generally at 22 and which will be later described in detail.

Figure 2:
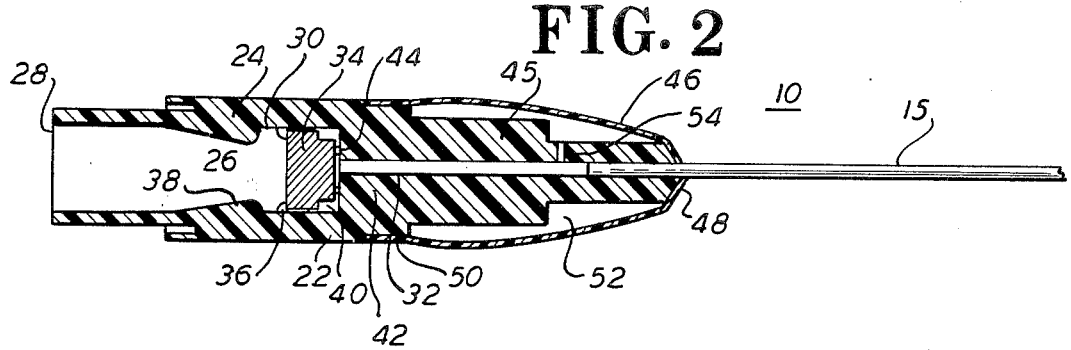
FIG. 2 is a longitudinal cross-sectional view of the molded valve means and pilot balloon of FIG. 1.
Figure 3:
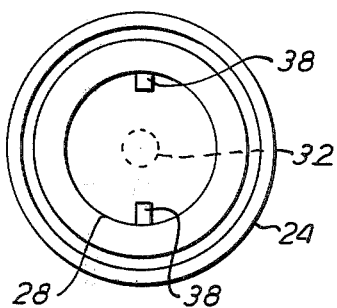
FIG. 3 is an enlarged end view of the inlet end of the valve shown in FIG. 2.

Turning now to FIG. 2, the inflating means 22 comprises a plastic valve housing 24 which is easily molded in one operation relatively flexible vinyl plastic material. The housing 24 has a main passageway 26 through which gas introduced at the housing inlet 28 can pass, as will be explained. As shown, the main passageway 26 has a relatively large diameter internal surface 30 but is reduced to a small diameter passage 32 within the housing 24.

A plug means 34 is positioned within the internal surface 30 and has its outer periphery inserted in an interference fit within the passageway 26 in sealing engagement with internal surface 30 to normally prevent the passage of gas in the main passageway 26 past the plug means 34. The plug means 34 is preferably a metal or plastic cylinder which is held in position, as shown, by a small circular bead 36 molded within the internal surface 30.

A radially inwardly projection 38 is molded to the internal surface 30 adjacent the plug means 34.

The projection 38 has a generally inwardly sloping surface to receive the external tip of a syringe which is inserted within inlet 28 when it is desired to either inflate or deflate the main cuff 18. As the top of the syringe is forced against projection 38, the resilient wall surrounding the plug means 34 is forced outwardly and a bypass passageway is created to allow gas to freely pass around the plug means 34 into or from the small diameter passage 32. As may be easily seen, when the syringe tip is removed from projection 38, the resilient wall will again close into sealing engagement with the plug means 34 and thus close main passageway 26. In the preferred form, a plurality of projections 38 may be formed on the internal surface 30.

Also, in order to assure unimpeded flow of gas by the plug means 34 when the syringe is in operative position, a portion of the plug means 34 may be recessed, as at 40. A means is provided to prevent the plug from sealing against the end 42 of the main passageway 26 and may include a plurality of molded tips 44, or in the alternate, a plurality of recesses may be formed in the plug means 34 adjacent the passageway end 42.

The plastic valve housing 24, in its preferred form has a tubular plastic extension 45 which is molded in one unitary piece. The pilot balloon 46 surrounds the tubular extension 45 and is sealed at its ends 48 and 50 to the extension 45, creating a gas-tight chamber 52 therewithin. A stub passageway 54 provides gas communication between the small diameter passage 32 and the chamber 52. At the end of the extension 45 the capillary tube 15 communicates with and is joined to the small diameter passage 32 so that the gas within chamber 52 is generally at the same pressure as within the main cuff 18. As the cuff 18 is inflated therefore, the pilot balloon 46 will also inflate and in similar manner deflation of both balloons is simultaneous.

Both the material comprising main cuff 18, and that comprising pilot balloon 46, is preferably a thin plastic, e.g. a urethane or vinyl having a thickness of about 0.002 to 0.010. inches. In both instances, the cuff and the pilot balloon are pre-stretched in a longitudinal direction prior to securing the end portions of the cuff or the pilot balloon to the tube portions or other elements to which the said ends are affixed.

Referring particularly to FIG. 1, it is thus seen that cuff 18 is pre-stretched longitudinally, i.e. between its end portions 17 and 19 prior to securing end portions 17 and 19 to tube 12. Because of the stressing introduced too the balloon by the pre-stretched condition, a series of longitudinally directed folds 21 are formed. These folds 21 are seen to extend in approximately parallel, and spaced relationship with respect to one another between the opposed end portions 17 and 19.

Figure 4:
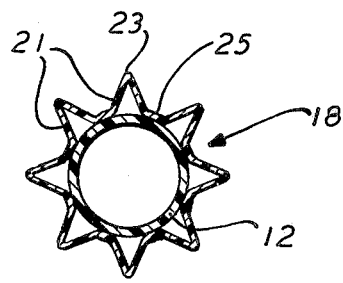
FIG. 4 is a transverse cross-section through the main cuff of the FIG. 1 device, the view being taken along the line 4—4 of FIG. 1.

As may be seen from consideration of the cross-sectional view of FIG. 4, taken along the line 4—4 FIG. 1, each of the folds 21 effectively defines a ridge 23, which substantially extends in continuous fashion between the opposed end portions 17 and 19. In between each of the ridges 23, a trough-like portion 25 is defined, which may substantially reside adjacent the tube 12 surface. These troughs too, extend in substantially continuous fashion between the end portions 17 and 19 of the cuff.

The folds 21 effected by the pre-stretched condition are, as mentioned, essentially oriented in a longitudinal direction; and the cuff 18 in its non-inflated condition is, further substantially devoid of random folds, and especially is devoid of folds oriented in a transverse direction with respect to the axis of tube 12. The net result of this arrangement is that the folds 21 of cuff 18 are oriented in the same direction in which tube 10 is inserted into the patient's trachea. This is to say, that substantially all folds are oriented as "streamlines" with respect to the direction of tracheal insertion. Accordingly cuff 18 includes substantially no portions, such as transverse folds, which would impede insertion of the tracheal tube 10 into the patient's trachea.

It will further be evident that the absence of such transverse or random folds, assures that upon the tube coming to rest within the trachea, no portions thereof are likely to be bunched up as a result of tube insertion. In consequence, upon subsequent inflation of cuff 18, effective seating of same with the walls of the trachea is assured.

In a precisely analagous fashion to the structure that has just been described with reference to cuff 18, the pilot balloon 46 is similarly pre-stretched longitudinally; and the ends 48 and 50 thereof are secured to extension 45 in the pre-stretched condition. The configuration of folding developed at the surface of pilot balloon 46 is accordingly essentially identical to that described in connection with cuff 18; and in order to emphasize this point, corresponding reference numerals have been applied to the folds 21 at the pilot balloon 46. In this instance, however, the folds 21, as indicated, extend between the secured end portions 48 and 50. Similarly, it will be evident that the cross-sectional view of FIG. 4 is substantially identical to a median cross-section taken through the axis of pilot balloon 46, except for the scale of same.

In the case of pilot balloon 46, the longitudinally directed folds 21 serve, however, a completely dissimilar function. In particular in this instance, the ridges 23 and alternating troughs 25, serve to perform a visual indication function. In particular, the said ridges 23 of folds 21, markedly contrast with the troughs 25 between folds, to thereby constitute a series of spaced highly visible markings extending between the end portions 48 and 50 of the pilot balloon. These markings serve to graphically signal to an observer the non-inflated condition of the pilot balloon, and, in turn, indicates to such observer a corresponding condition for cuff 18.

In securing the balloon 46 to the extension 45, the balloon is stretched longitudinally and the ends are secured to extension 45 in the stretched condition. It is therefore essential that the extension 45 be solid or unbroken through the entire length of balloon 46 to maintain the pre-stretch and provide support. Due to the pre-stretch introduced into a balloon of this thinness, the balloon assumes the characteristic state discussed and its deflated condition is readily apparent. The characteristic appearance is also believed to be enhanced by providing a balloon which is secured at its ends to the extension 45 having different diameters, that is, one end of the balloon 45 is secured to a relatively large diameter surface of extension 45, while the other end is secured to a smaller diameter surface of the extension 45. The resulting pilot balloon 46 is extremely sensitive to internal gas pressure and the condition of the cuff 18 can be determined easily by visual indication of the pilot balloon 46.

Figure 5:
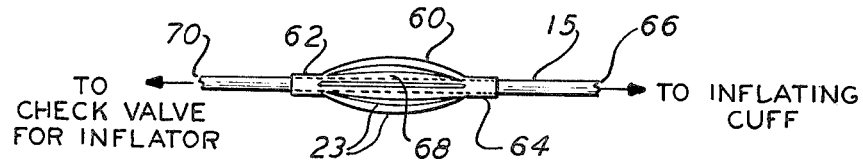
FIG. 5 is a perspective partial view of a gas-inflating passageway forming part of a further endotracheal tube construction, to which is secured a further pilot balloon in accordance with the invention.

The visual indicating mechanism provided by the pre-stretched pilot balloon 46, can be utilized with other tracheal tube arrangements than that specifically illustrated in FIGS. 1 through 4. For example, in FIG. 5 hereof, a portion of a capillary tube 15, similar to tube 15 of FIG. 2 is shown. In this instance a pilot balloon 60 is secured to tube 15 in a pre-stretched condition in accordance with the principles previously set forth. The balloon 60 thus has opposed end portions 62 and 64, which in this instance are of the same diameter, unlike the configuration described in connection with FIGS. 1 through 4. One end 66 of tube 15 extends to an inflation cuff in accordance with constructions previously described; and the pressure within the said cuff is communicated to the interior of the pilot balloon through an opening 68 in the tube portion which passes through the expandable center of pilot balloon 60. The tube 15 is connected at its opposite end 70, to a conventional check valve means, which may be connected to an inflater. The check valve means in the present instance is assumed here to be of a conventional type, e.g. such as are shown in U.S. Pat. Nos. 3,352,531; 3,409,015; 3,577,992 and 3,726,282, and in other prior art locations.

While the present invention has been particularly set forth in terms of specific embodiments thereof, it will be understood in view of the present disclosure, that numerous variations upon the invention are now enabled to those skilled in the art, which variations yet reside within the scope of the present teaching. Accordingly the invention is to be broadly construed, and limited only by the scope and spirit of the claims now appended hereto.

I claim:

1. A tracheal tube adapted for insertion into the trachea of a patient for introducing and removing gas, said tube having a main inflatable chamber surrounding the distal end thereof, a gas passageway having one end communicating with the interior of said main inflatable chamber and having the other end adapted to receive an inflating means for delivering gas to inflate said main inflatable chamber; said gas passageway including a valve means for selectively introducing gas through said passageway to said inflatable chamber and a pilot balloon means comprising a tubular extension, a flexible oval-shaped pilot balloon having its outer ends secured to said tubular extension, thereby forming an enclosed pilot chamber; said pilot chamber being in gas communication with said main inflatable chamber through said gas passageway and an opening provided in said tubular extension; and said flexible pilot balloon being secured to said tubular extension in a pre-stretched condition along its length, whereby said balloon is characterized in a non-inflated condition by a series of spaced folds extending longitudinally between said secured ends, and is substantially free of transversely oriented folds, the ridges of said longitudinal folds contrasting with the troughs between said folds to constitute a series of spaced visually discernible markings between said secured ends to thereby visually signal said non-inflated condition of said balloon and the corresponding inflation condition of said main chamber.

2. A device in accordance with claim 1, wherein said flexible oval-shaped balloon has outer ends of different diameters secured to said tubular extension.

3. A device in accordance with claim 1, wherein said pilot balloon is a plastic material having a thickness of from about 0.002 to 0.010 inches.

4. A tracheal tube in accordance with claim 1, wherein said main inflatable chamber comprises a second flexible oval-shaped balloon having outer open ends secured to said tracheal tube, in a longitudinally pre-stretched condition, whereby said second balloon is characterized in the non-inflated state by a series of longitudinally extending folds and is substatially free of folds oriented transverse to said longitudinal direction, whereby said non-inflated balloon is streamlined in the direction of said tracheal insertion to facilitate said insertion.

5. A tracheal tube adapted for insertion into the trachea of a patient for introducing and removing gas, said tube having an inflatable cuff surrounding the distal end thereof; a gas passageway having one end communicating with the inertior of said inflatable cuff, and having the other end adapted to receive an inflating means for delivering gas to inflate said cuff; said gas passageway including check valve means for selectively introducing gas through said passageway to said cuff; and a generally oval pilot balloon means intermediate said check valve means and said inflatable cuff and being in communication with the interior of said cuff via said gas passageway, to indicate the state of expansion thereof; said pilot balloon being longitudinally pre-stretched between its opposite ends by mseans maintaining said longitudinally pre-stretched condition, with the pilot balloon portions between said ends being free to expand to signal said cuff condition; whereby said pilot balloon is characterized in the non-inflated condition by a series of spaced folds extending longitudinally between said opposed ends and is substantially free of transversely oriented folds, the ridges of said folds contrasting with the troughs between folds to constitute a series of spaced, visually discernible markings extending between said ends to thereby visually signal said non-inflated condition of said pilot balloon and the corresponding conditions of said cuff.

6. A device in accordance with claim 5, wherein said pilot balloon comprises a plastic material having a thickness of from about 0.002 to 0.010 inches.

* * * * *

UNITED STATES PATENT AND TRADEMARK OFFICE
CERTIFICATE OF CORRECTION

PATENT NO. : 4,018,231
DATED : April 19, 1977
INVENTOR(S) : Dean R. Wallace

It is certified that error appears in the above-identified patent and that said Letters Patent are hereby corrected as shown below:

Col. 1, line 6, "8" should read -- 26 --.

Col. 4, line 49, after "operation" the word -- of -- should be inserted.

Col. 8, line 7, after "outer" the word -- open -- should be inserted;

line 18, "substatially" should read -- substantially --;

line 27, "inertior" should read -- interior --;

line 37, "mseans" should read -- means --.

Signed and Sealed this twelfth Day of July 1977

[SEAL]

Attest:

RUTH C. MASON
*Attesting Officer*

C. MARSHALL DANN
*Commissioner of Patents and Trademarks*